(12) United States Patent
Kang et al.

(10) Patent No.: US 10,088,595 B2
(45) Date of Patent: Oct. 2, 2018

(54) SYSTEMS AND METHODS FOR INSPECTING AN AIRCRAFT

(71) Applicants: Tsinghua University, Haidian District, Beijing (CN); Nuctech Company Limited, Haidian District, Beijing (CN)

(72) Inventors: Kejun Kang, Beijing (CN); Jianmin Li, Beijing (CN); Jingyu Gu, Beijing (CN); Yuanjing Li, Beijing (CN); Yulan Li, Beijing (CN); Yaohong Liu, Beijing (CN); Zhen Tan, Beijing (CN); Yucheng Wu, Beijing (CN); Weizhen Wang, Beijing (CN)

(73) Assignees: Tsinghua University, Haidian District, Beijing (CN); Nuctech Company Limited, Haidian District, Beijing (CN)

( * ) Notice: Subject to any disclaimer, the term of this patent is extended or adjusted under 35 U.S.C. 154(b) by 665 days.

(21) Appl. No.: 14/399,566

(22) PCT Filed: Jul. 31, 2014

(86) PCT No.: PCT/CN2014/083366
§ 371 (c)(1),
(2) Date: Nov. 7, 2014

(87) PCT Pub. No.: WO2015/051665
PCT Pub. Date: Apr. 16, 2015

(65) Prior Publication Data
US 2016/0258884 A1    Sep. 8, 2016

(30) Foreign Application Priority Data
Oct. 12, 2013   (CN) .......................... 2013 1 0476261

(51) Int. Cl.
*G01V 5/00*   (2006.01)
*G01N 23/04*  (2018.01)
(Continued)

(52) U.S. Cl.
CPC .............. *G01V 5/0066* (2013.01); *B64F 5/60* (2017.01); *G01N 23/04* (2013.01); *G01V 5/0016* (2013.01);
(Continued)

(58) Field of Classification Search
CPC .. H05G 1/00; H05G 1/02; H05G 1/04; H05G 1/56; G01N 23/00; G01N 23/02;
(Continued)

(56) References Cited

U.S. PATENT DOCUMENTS

| 5,014,293 A | 5/1991 | Boyd et al. |
| 5,903,623 A * | 5/1999 | Swift ..................... G01N 23/04 378/198 |

(Continued)

FOREIGN PATENT DOCUMENTS

| CN | 1133440 A | 10/1996 |
| CN | 102551744 A | 7/2012 |

(Continued)

OTHER PUBLICATIONS

Extended European Search Report for corresponding European Patent Application No. 14786438.3 dated Nov. 20, 2015.

(Continued)

*Primary Examiner* — Anastasia Midkiff
(74) *Attorney, Agent, or Firm* — Merchant & Gould P.C.

(57) ABSTRACT

The present disclosure provides a system and method for inspecting an aircraft. An X-ray/Gamma ray radiation source and a detector are located at above and below a fuselage of an aircraft, respectively. The X-ray/Gamma ray radiation source emits a beam of radiation[ ], wherein the X-ray/Gamma ray radiation[ ] passes through the aircraft to be inspected. The detector receives and converts the beam of X-ray/Gamma ray radiation[ ] that has passed through the
(Continued)

aircraft to an output signal, and the system generates a vertical transmission image in real time.

15 Claims, 3 Drawing Sheets

(51) Int. Cl.
*B64F 5/60* (2017.01)
*H01J 37/02* (2006.01)
*H01L 27/146* (2006.01)
*G01N 23/10* (2018.01)

(52) U.S. Cl.
CPC ........ *H01L 27/14618* (2013.01); *G01N 23/10* (2013.01); *G01N 2223/631* (2013.01); *H01J 37/023* (2013.01)

(58) Field of Classification Search
CPC ........ G01N 23/04; G01N 23/06; G01N 23/08; G01N 23/083; G01N 23/087; G01N 23/10; G01N 23/18; G01N 2291/26; G01N 2291/269; G01N 2291/2694; G01N 2223/00; G01N 2223/03; G01N 2223/04; G01N 2223/10; G01N 2223/1006; G01N 2223/101; G01N 2223/1013; G01N 2223/1016; G01N 2223/20; G01N 2223/30; G01N 2223/308; G01N 2223/33; G01N 2223/3302; G01N 2223/3303; G01N 2223/3305; G01N 2223/3307; G01N 2223/3308; G01N 2223/40; G01N 2223/413; G01N 2223/42; G01N 2223/423; G01N 2223/50; G01N 2223/501; G01N 2223/5015; G01N 2223/502; G01N 2223/505; G01N 2223/5055; G01N 2223/60; G01N 2223/624; G01N 2223/628; G01N 2223/629; G01N 2223/63; G01N 2223/631; G01N 2223/646; G01N 2223/648; G01V 5/00; G01V 5/0008; G01V 5/0016; G01V 5/0033; G01V 5/0041; G01V 5/005; G01V 5/0066; G01B 15/00; G01B 15/06; G01B 15/08; G01B 21/28; G01B 21/30; E04H 6/44; B63F 5/00; B63F 5/60; H01J 35/00; H01J 35/02; H01J 35/025; H01J 35/16; H01J 37/00; H01J 37/02; H01J 37/023; H01J 37/16; H01J 37/20; H01J 37/244; H01J 2235/00; H01J 2235/16; H01J 2235/161; H01J 2235/163; H01J 2237/00; H01J 2237/02; H01J 2237/024; H01J 2234/0245; H01J 2237/06; H01J 2237/061; H01J 2237/16; H01J 2237/20; H01J 2237/202; H01J 2237/20221; H01J 2237/20235; H01J 2237/20278; H01J 2237/20285; H01J 2237/20292; H01J 2237/204; H01J 2237/244; H01J 2237/2441; H01J 2237/24415; H01J 2237/2446; H01J 2237/24465; H01J 2237/2447; H01L 27/146; H01L 27/14601; H01L 27/14618; G05B 2219/40293; G05B 2219/39; G05B 2219/39001; G05B 2219/39004; G05B 2219/40205; G05B 2219/40235; G05B 2219/50389; G05B 2219/50228; B64F 5/00; B64F 5/60
See application file for complete search history.

(56) References Cited

U.S. PATENT DOCUMENTS

| | | | | |
|---|---|---|---|---|
| 7,722,251 | B2* | 5/2010 | Kang | G01V 5/0008 378/10 |
| 8,345,819 | B2* | 1/2013 | Mastronardi | G01V 5/0008 378/198 |
| 8,503,605 | B2* | 8/2013 | Morton | G01V 5/0016 378/57 |
| 8,923,478 | B2* | 12/2014 | Knight | G01N 23/18 250/257 |
| 2006/0198498 | A1* | 9/2006 | Birdwell | G01N 23/04 378/204 |
| 2008/0156992 | A1* | 7/2008 | Kang | G01V 5/0016 250/359.1 |
| 2009/0060128 | A1* | 3/2009 | Kang | G01V 5/005 378/57 |
| 2009/0060129 | A1* | 3/2009 | Kang | G01V 5/0008 378/57 |
| 2011/0026673 | A1* | 2/2011 | Mastronardi | G01V 5/0008 378/57 |
| 2011/0064192 | A1* | 3/2011 | Morton | G01V 5/0016 378/57 |
| 2011/0103548 | A1 | 5/2011 | Bendahan | |

FOREIGN PATENT DOCUMENTS

| | | |
|---|---|---|
| CN | 102686999 A | 9/2012 |
| CN | 102834738 A | 12/2012 |
| CN | 103529480 A | 1/2014 |
| CN | 203490377 U | 3/2014 |
| GB | 2 420 682 A | 5/2006 |
| RO | 127988 | 11/2012 |

OTHER PUBLICATIONS

International Search Report for corresponding International Patent Application No. PCT/CN2014/083366 dated Sep. 29, 2014.
European Office Action for corresponding European Patent Application No. 14786438.3 dated May 12, 2017, 4 pages.
European Office Action for corresponding European Patent Application No. 14786438.3 dated Oct. 19, 2017, 5 pages.

* cited by examiner

SYSTEMS AND METHODS FOR INSPECTING AN AIRCRAFT

TECHNICAL FIELD

The embodiments of the present invention generally relate to security inspection systems and methods for inspecting aircrafts using rays.

BACKGROUND

Currently there is no such scanning system that is specially defined for inspecting aircrafts. Among the existing security inspection systems that use X-rays or Gamma-rays, only scanning systems that base on the backscatter technology can be used to scan aircrafts. The backscatter technology is to place a ray source and a detector at a same side of an object to be inspected, so that X-rays or Gamma-rays emitted from the ray source reach the object to be inspected, with some particles absorbed by the object to be inspected, while particles that have not been absorbed scatter at the object. Scattered particles transmit through the object to be inspected if the scattering angle is smaller than 90 degrees; while scattered particles are reflected from the incidence side if the scattering angle is larger than 90 degrees. The backscatter principle is to place a ray source and a detector at a same side of an object to be inspected and to detect back scattered particles that are scattered with a scattering angle larger than 90 degrees.

The backscatter based products occupy less area and can be used flexibly. Such scanning systems, however, are not designed dedicatedly for aircraft inspection, and thus have some defects if they are used in aircraft inspection. The backscatter scanning systems have rays of a low energy that cannot penetrate a wing and a fuselage to perform a complete and thorough inspection. In the case that the object is of a low Z material at the portion close to the location where the ray source is located, the rays are scattered with a larger angle at the low Z material, and a lot of particles are reflected and cannot penetrate into the interior of the object to be inspected, and thus a thorough inspection cannot be done. When it comes to an aircraft inspection, the backscatter based products typically is on a mobile on-board platform, and cannot inspect all the portions of an aircraft, e.g., the portions that are far away from the ground (such as a wing) or too close to the ground (such as bottom of a business aircraft). Furthermore, the scanning efficiency of the on-board backscatter scanning systems is low since they need to move along the fuselage and the lateral wings during the scanning of an aircraft.

SUMMARY

In view of one or more problems of the prior art, systems for inspecting an aircraft are provided.

According to an aspect of the invention, there is provided an aircraft inspection system comprising: a portal-framed structure; a radiation source configured to emit a beam of radiations, and being mounted and movable on the bar of the portal-framed structure; a detector configured to receive and convert the beam of radiations to an output signal, and being arranged in a trench that is co-planar with the beam of radiations emitted from the radiation source; a controller connected to the detector and the radiation source and configured to control the radiation source to emit a beam of radiations when an aircraft to be inspected moves through a scanning region constituted by the radiation source and the detector, and to control the detector to receive a beam of radiations emitted from the radiation source that has passed through the inspected aircraft; and an image generation module configured to receive the output signal from the detector and generate a vertical transmission image of the inspected aircraft.

Preferably, the portal-framed structure has a rail on the bar to allow the radiation source moving along the rail, and the detector moves along a rail in the trench in synchronization to the radiation source. The controller is further configured to control the radiation source to move to a predetermined position at a side along the rail, and control the detector to move to a position corresponding to the predetermined position at the side synchronously, so that a transmission inspection can be performed on the side of the inspected aircraft.

Preferably, the detector has a length less than or equal to half of a width of the portal-framed structure.

Preferably, the radiation source is an accelerator or a radioactive source that generates X-rays or Gamma-rays.

Preferably, the detector comprises a gas detector or a solid detector sensitive to X-rays or Gamma-rays.

Preferably, the detector is fixed in the trench.

Preferably, the portal-framed structure has a rail to allow the radiation source to move along the rail; the controller controls the radiation source to move along the rail to a side, so that a transmission inspection can be performed on the side of the inspected aircraft.

Preferably, the detector has a length larger than or equal to two thirds of a width of the portal-framed structure.

Preferably, the radiation source emits a first beam of radiations having a first energy and a second beam of radiations having a second energy. The detector receives the first and second beams of radiations. The image generation module receives the output signal from the detector and generates a dual-energy transmission image of the inspected aircraft.

Preferably, the detector comprises a first array of detectors that respond to a first portion of a beam of radiations and a second array of detectors that respond to a second portion of the beam of radiations and are arranged under the first array of detector. The image generation module receives the output signals of the first and second arrays of detectors and generates a dual-energy transmission image of the inspected aircraft.

Preferably, the radiation source emits a beam of first-angle radiations and a beam of second-angle radiations. The detector comprises an array of first-angle detectors and an array of second-angle detectors that receive a beam of first-angle radiations and a beam of second-angle radiations that pass through the inspected aircraft, respectively, the array of first-angle detectors and the array of second-angle detectors each being arranged in respective trenches at a predetermined interval substantially parallel to the bar of the portal-framed structure. The image generation module receives the output signals from the array of first-angle detectors and the array of second-angle detectors and generates dual-view transmission images of the inspected aircraft.

Preferably, the portal-framed structure has a height that is adjustable.

According to another aspect of the invention, there is provided an aircraft inspection method, comprising steps of: emitting a beam of radiations from a radiation source which is mounted on a portal-framed structure; receiving and converting the beam of radiations to an output signal by a detector arranged in a trench that is co-planar with the beam of radiations emitted from the radiation source; controlling the radiation source to emit a beam of radiations when an aircraft to be inspected moves through a scanning region constituted by the radiation source and the detector, and controlling the detector to receive a beam of radiations emitted from the radiation source that has passed through the inspected aircraft; and receiving the output signal from the detector to generate a vertical transmission image of the inspected aircraft.

Preferably, the method further comprises steps of controlling the radiation source to move to a predetermined position at a side along a rail on the bar, and controlling the detector to move to a position corresponding to the predetermined position at the side synchronously, so that a transmission inspection can be performed on the side of the inspected aircraft.

According to yet another aspect of the invention, there is provided a system for inspecting an aircraft, comprising: a portal-framed structure comprising a support and a bar on the support; at least two radiation sources configured to emit a beam of radiations, the at least two radiation sources being mounted on a portal-framed structure and emitting beams of radiations that are co-planar with each other; a detector configured to receive and convert the beam of radiations to an output signal, which is arranged in a trench that is co-planar with the beam of radiations emitted from the radiation sources; a controller connected to the detector and the at least two radiation sources and configured to control the at least two radiation sources to emit a beam of radiations when an aircraft to be inspected moves through a scanning region constituted by the at least two radiation sources and the detector, and to control the detector to receive beams of radiations emitted from the at least two radiation sources that have passed through the inspected aircraft; and an image generation module configured to receive the output signal from the detector and generate a vertical (e.g., top-down) transmission image of the inspected aircraft.

According to the embodiments, a transmission inspection can be performed on an aircraft quickly and accurately.

BRIEF DESCRIPTION OF THE DRAWINGS

The implementations of the invention are illustrated in the drawings. The drawings and implementations provide some embodiments of the invention non-exclusively without limitation, where.

Figure 1:
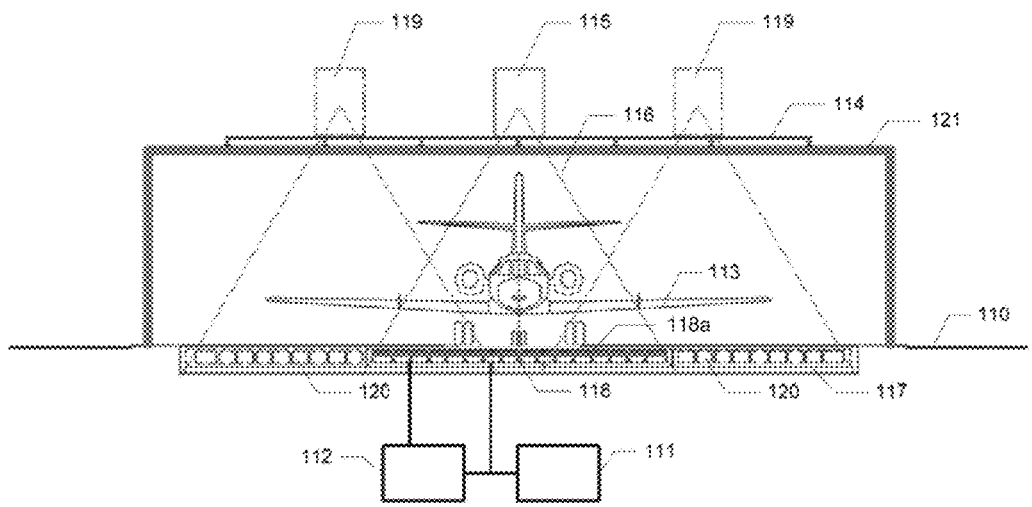
FIG. 1 illustrates a structural diagram of a system for inspecting an aircraft according to an embodiment of the invention.

REFERENCE SIGNS 110 ground
111 image generation module
112 controller
113 inspected aircraft
114 rail
115 radiation source
116 beam of radiations
117 trench
118 detector
118a detector cover
119 scanning positions after movement of the accelerator at both sides
120 positions after movement of the detector at both sides
121 portal-framed structure
122 beam of radiations
123 detector
124 beam of radiations
125 detector

DETAILED DESCRIPTION OF THE EMBODIMENTS

The particular embodiments of the invention are described below in details. It shall be noted that the embodiments herein are used for illustration only, but not limiting the invention. In the description below, a number of particular details are explained to provide a better understanding to the invention. However, it is apparent to those skilled in the art the invention can be implemented without these particular details. In other examples, well known circuits, materials or methods are not described so as not to obscure the invention.

Throughout the specification, the reference to "one embodiment," "an embodiment," "one example" or "an example" means that the specific features, structures or properties described in conjunction with the embodiment or example are included in at least one embodiment of the present invention. Therefore, the phrases "in one embodiment," "in an embodiment," "in one example" or "in an example" occurred at various positions throughout the specification may not refer to one and the same embodiment or example. Furthermore, specific features, structures or properties may be combined into one or several embodiments or examples in any appropriate ways. Moreover, it should be understood by those skilled in the art that the term "and/or" used herein means any and all combinations of one or more listed items.

According to some embodiments of the invention, a radiation source and a detector locate at above and below of a fuselage of an aircraft, respectively. The radiation source emits X-rays or Gamma-rays, which pass through the aircraft to be inspected. An array of detectors receives and converts the X-rays or Gamma-rays to an output signal, and generates a vertical (e.g., top-down) transmission image in real time.

FIG. 1 illustrates a structural diagram of a system 100 for inspecting an aircraft according to an embodiment of the invention. As shown in FIG. 1, the system 100 comprises a radiation source 115, a portal-framed structure 121, a detector 118, a controller 112 and an image generation module 111. The radiation source 115 may be for example an X-ray source or a Gamma-ray source that emits a beam of radiations 116. The detector 118 may include a gas or solid detector sensitive to X-rays or Gamma-rays. The portal-framed structure 121 bears the radiation source 115 on the portal-framed structure 121, so that the radiation source 115 emits beams of X-rays downward. The detector 118 is arranged in a trench that is co-planar with the beam of radiations emitted from the radiation source, such as the trench on the ground 110 shown in FIG. 1.

The controller 112 is connected to the detector 118 and the radiation source 115, and controls the radiation source 115 to emit a beam of radiations. When inspecting, an aircraft 113 moves through a scanning region constituted by the radiation source and the detector, and the controllers controls the detector to receive a beam of radiations emitted from the radiation source 115 that has passed through the inspected aircraft 113 so as to obtain an output signal. Image generation module 111 may be for example an imaging computer which receives the output signal and generates a vertical transmission image of the inspected aircraft 113 based on the output signal.

According to the illustrated embodiment, portal-framed structure 121 is provided with a rail 114 to allow the radiation source 115 moving along rail 114 to locations 119 at the left or at the right. The detector 118 moves along a rail in the trench to a corresponding position 120 at the left or at the right in synchronization to the radiation source 115. In such a case, the controller 120 controls the radiation source 115 to move to a side along the rail 114, and controls the detector 118 to move to the side synchronously, so that a transmission inspection can be performed on the side of the inspected aircraft 113.

In such a way, the synchronization can be easily controlled since the radiation source and the detector move linearly along rails in the same direction, such as a direction perpendicular to the movement direction of the aircraft. Furthermore, the detector is arranged in a trench so that the aircraft may move on the protective plate 118a covering the detector, and thereby the time required for scanning is reduced.

Moreover, the detector is arranged in a trench so that the surface of the detector or the top surface of the cover plate 118a of the detector is co-planar with the ground. When the aircraft moves above the detector, it can move stably without any fluctuation. Also, in the process of scanning and inspecting, the radiation source and the detector may move synchronously without any difficulty, so that the wing of the aircraft or even an aircraft of a large volume can be inspected quickly.

According to the embodiment, in the process of scanning the inspected aircraft 113, the radiation source 115 generates pulsed X-rays or Gamma-rays of a high energy which can penetrate the inspected aircraft 113, and the high energy sensitive detectors receive and convert the X-rays or Gamma-rays to an output signal. After the whole scanning process is finished, the image generation module 111 automatically generates a complete transmission image of the inspected aircraft.

The radiation source used in the embodiment may be a linear accelerator (or other types of radiation sources) which is fixed in the air by a steel support, while the array of detectors are placed in a trench that is co-planar with the beam of radiations from the radiation source. When the aircraft is an unmanned aircraft, a pulling device will drag the aircraft to move through a beam of radiations and shall cause no damage to the aircraft. The detector receives X-rays or Gamma-rays that have passed through the aircraft (e.g. attenuated by the inspected aircraft) and convert them to an output signal. When the whole scanning process is finished, the image generation module 111 generates a vertical scan image of the aircraft. In the case that the beam field angle of the radiation source cannot cover the whole aircraft at the same time, in order to scan the whole aircraft (including fuselage, wings and tail), the radiation source 115 and the detector 118 may move at the steel support and in the trench in a direction perpendicular to the movement direction of the aircraft, respectively, being stationary relative to each other, so as to scan different portions of the aircraft. The radiation source 115 scans the aircraft at one, two or even more positions (such as the three positions shown in FIG. 1), so as to scan the whole aircraft. The detector moves in synchronization to the radiation source, so that it is always at a corresponding position under the radiation source[ ]. In the embodiment of FIG. 1, by taking the trade-off between the cost of the detector and the number of round trips for scanning the aircraft into account, the length of the detector may be set to be smaller than or equal to a half of the width of portal-framed structure 121. For example, the length of the detector may be set to be one third or one quarter of the width of portal-framed structure 121. In the case that the detector has a length that is far smaller than the width of the portal-framed structure, the whole aircraft can be scanned and inspected by increasing the number of round trips for scanning the aircraft.

Figure 2:
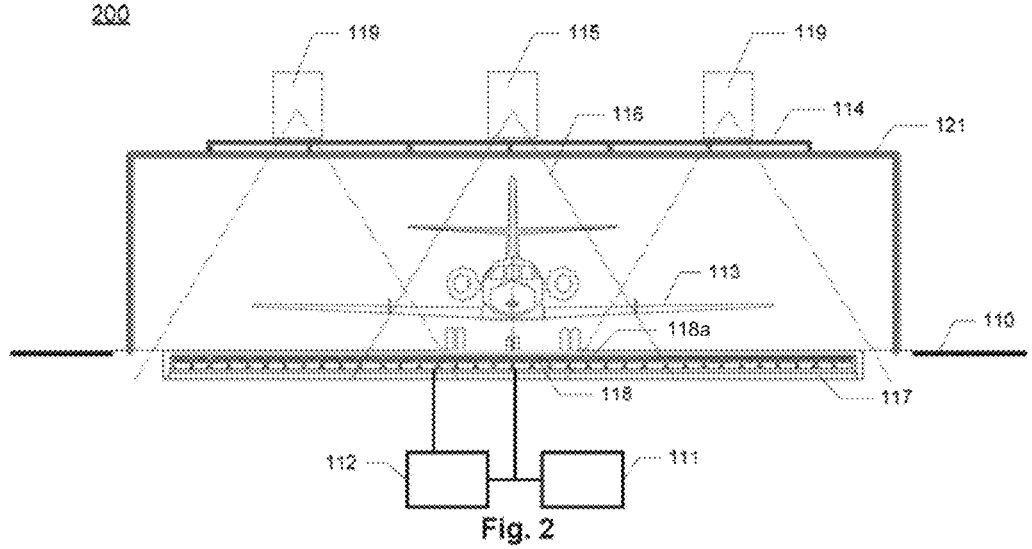
FIG. 2 illustrates a structural diagram of a system for inspecting an aircraft according to another embodiment of the invention.

FIG. 2 illustrates a structural diagram of a system 200 for inspecting an aircraft according to another embodiment of the invention. In the embodiment shown in FIG. 2, the detector 118 is entirely fixed in the trench 117 without any sliding in the trench. In such a case, since the detector is fixed in the trench without any sliding, the length of the detector is set to be larger than or equal to two thirds of the width of the portal-framed structure 121 or even substantially equal to the width of the portal-framed structure, so that a transmission scanning can be performed on the whole aircraft. In the shown embodiment, only the radiation source 115 laterally moves to positions 119 at both sides as required, so that a transmission scanning can be performed on the whole aircraft.

Figure 3:
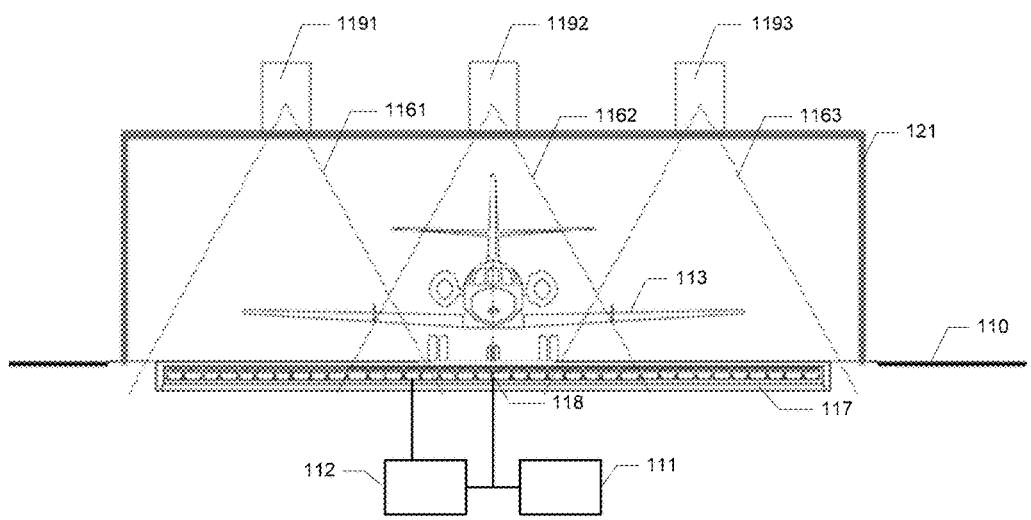
FIG. 3 illustrates a structural diagram of a system for inspecting an aircraft according to yet another embodiment of the invention.

FIG. 3 illustrates a structural diagram of a system 300 for inspecting an aircraft according to yet another embodiment of the invention. In the shown embodiment, in order to accelerate the inspecting process, three radiation sources 1191, 1192, and 1193 are arranged on the support that are co-planar with the beam of radiations and emit beams of X-rays or beams of Gamma-rays 1161, 1162, and 1163 downward. The system for inspecting an aircraft shown in the figure comprises to three radiation sources 1191, 1192, and 1193, portal-framed structure 121, the detector 118 in the trench 117, the controller 112, and the image generation module 11. In the embodiment as shown, the portal-framed structure 121 bears the three radiation sources. The beams of radiations emitted from the radiation sources are co-planar with each other, and correspond to the detector in the trench.

The detector 118 is set in the trench 117 that is co-planar with the beams of radiations emitted from the radiation sources. The controller 112 is connected to the detector and the three radiation source, to control the three radiation sources to emit a beam of radiations when an aircraft to be inspected moves through a scanning region constituted by the three radiation sources and the detector, and to control the detector to receive beams of radiations emitted from the three radiation sources that have passed through the inspected aircraft, so as to obtain an output signal. The image generation module 111 receives the output signal and generates a vertical transmission image of the inspected aircraft based on the output signal.

The embodiment may accelerate the speed of security inspection for aircrafts. The whole fuselage is scanned after the aircraft passes the scanning region once.

In other embodiments, those skilled in the art may use more or less radiation sources in different cases.

Figure 4:
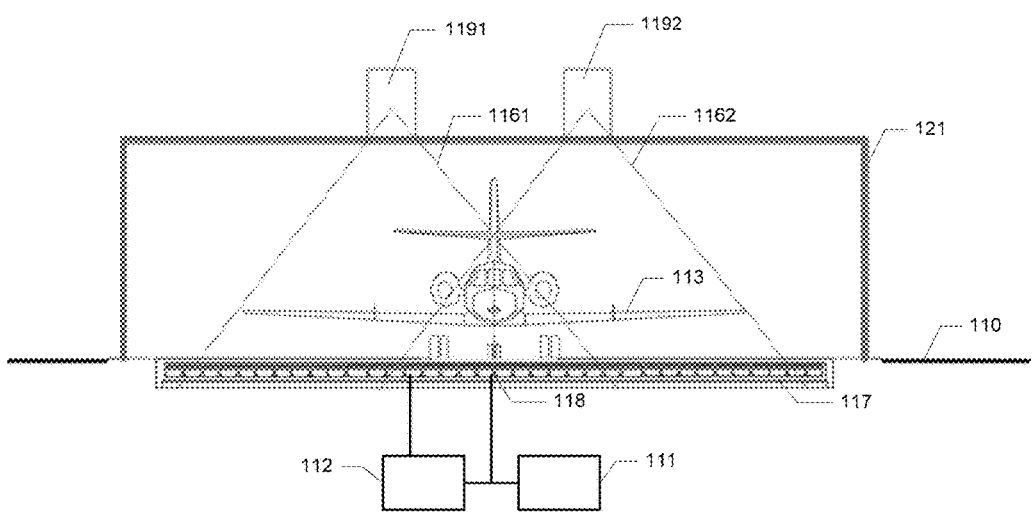
FIG. 4 illustrates a structural diagram of a system for inspecting an aircraft according to still another embodiment of the invention.

FIG. 4 illustrates a structural diagram of a system 400 for inspecting an aircraft according to still another embodiment of the invention. Only two radiation sources 1191 and 1192 are used in the embodiment shown in FIG. 4, so as to reduce the cost.

In some embodiment, the radiation source 115 emits a first beam of radiations having a first energy such as a beam of low-energy radiations of 3 MeV and a second beam of radiations having a second energy such as a beam of high-energy radiations of 6 MeV or 9 MeV. The detector 118 receives the first and second beams of radiations. In such a case, the image generation module 111 receives the output signals from the first and second arrays of detectors and generates a dual-energy transmission image of the inspected aircraft 113. In such a case, the image generation module 111 outputs a dual-energy image of the inspected aircraft.

In some embodiments, the detector 118 comprises a plurality of arrays of detectors that respond to different portions of a beam of radiations, such as a first array of detectors that respond to a first portion (e.g., the portion of a low energy) of a beam of radiations and a second array of detectors that respond to a second portion (e.g., the portion of a high energy) of the beam of radiations and are arranged under the first array of detector. In such a case, the image generation module 111 receives the output signals of the first and second arrays of detectors and generates a dual-energy transmission image of the inspected aircraft 113. In such a case, the image generation module 111 outputs a pseudo dual-energy image of the inspected aircraft.

Figure 5:
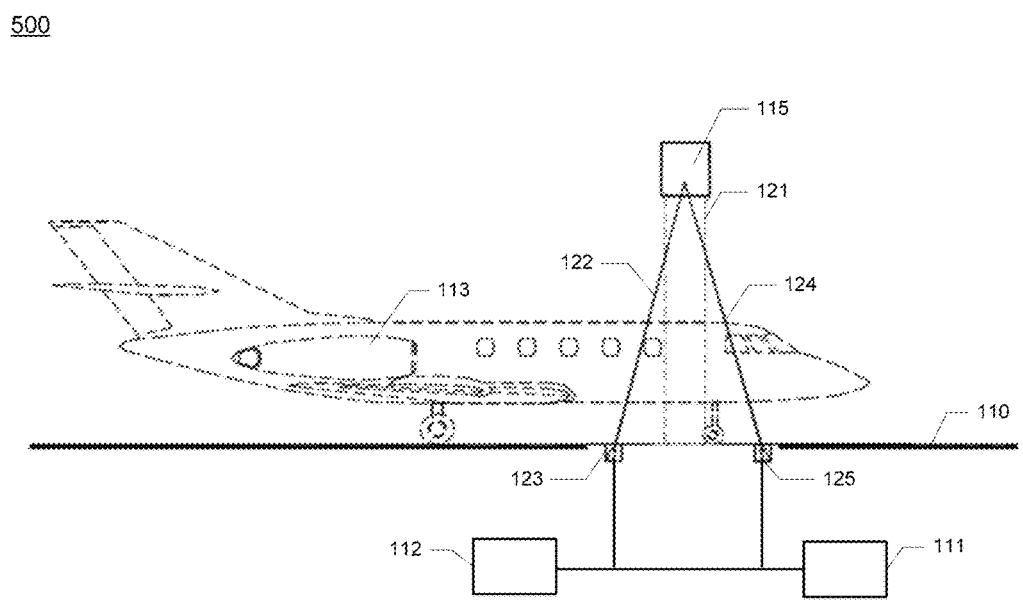
FIG. 5 illustrates a structural diagram of a system for inspecting an aircraft according to other embodiments of the invention.

FIG. 5 illustrates a structural diagram of a system 500 for inspecting an aircraft according to other embodiments of the invention. In the embodiment as shown in FIG. 5, the radiation source 115 emits a beam of first-angle radiations 122 and a beam of second-angle radiations 124. The detector comprises an array of first-angle detectors 123 and an array of second-angle detectors 125 that receive the beam of first-angle radiations 122 and the beam of second-angle radiations 124 that pass through the inspected aircraft, respectively. The array of first-angle detectors 123 and the array of second-angle detectors 125 each are arranged in respective trenches at a predetermined interval substantially parallel to the portal-framed structure 121. The image generation module 111 receives the output signals from the array of first-angle detectors 123 and the array of second-angle detectors 125 and generates dual-view transmission images of the inspected aircraft 113, for example one transmission image under a first view and another transmission image under a second view.

The foregoing detailed description has set forth various embodiments of the system and method for inspecting an aircraft via the use of block diagrams, flowcharts, and/or examples. Insofar as such block diagrams, flowcharts, and/or examples contain one or more functions and/or operations, it will be understood by those skilled in the art that each function and/or operation within such examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of those skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present invention has been described with reference to several typical embodiments, it is apparent to those skilled in the art that the terms are used for illustration and explanation purpose and not for limitation. The present invention may be practiced in various forms without departing from the esprit or essence of the invention. It should be understood that the embodiments are not limited to any of the foregoing details, and shall be interpreted broadly within the esprit and scope as defined by the following claims. Therefore, Modifications and alternatives falling within the scope of the claims and equivalents thereof are to be encompassed by the scope of the present invention which is defined by the claims to as attached.

What is claimed is:

1. A system for inspecting an aircraft, comprising:
   a frame comprising a support;
   a radiation source configured to emit a beam of X-ray/Gamma ray radiation, and being mounted and movable on the support of the portal-framed structure;
   a detector configured to receive and convert the beam of X-ray/Gamma ray radiation to an output signal, and being arranged in a trench that is co-planar with the beam of X-ray/Gamma ray radiation emitted from the radiation source, the detector further including a cover adapted to at least partially support an aircraft to be inspected;
   a controller connected to the detector and the radiation source, and configured to control the radiation source to emit a beam of X-ray/Gamma ray radiation as the aircraft to be inspected moves through a scanning region constituted by the radiation source and the detector, and to control the detector to receive a beam of X-ray/Gamma ray radiation emitted from the radiation source that has attenuated by the inspected aircraft; and
   an image generation module configured to receive the output signal from the detector and generate a vertical transmission image of the inspected aircraft.

2. The system according to claim 1, wherein the support of the frame comprises a rail to allow the radiation source moving along the rail, and the detector moves along a rail in the trench in synchronization to the radiation source, and
   wherein the controller being further configured to control the radiation source to move along the rail to a predetermined position corresponding to a portion of the aircraft, and to control the detector to move to a position corresponding to the predetermined position synchronously, so that a transmission inspection can be performed on the portion of the inspected aircraft.

3. The system according to claim 2, wherein the detector has a length less than or equal to a half of a width of the portal-framed structure.

4. The system according to claim 1, wherein the radiation source is an accelerator or a radioactive source that generates X-rays or Gamma-rays.

5. The system according to claim 1, wherein the detector comprises a gas type detector sensitive to X-rays or Gamma-rays.

6. The system according to claim 1, wherein the detector is fixed in the trench.

7. The system according to claim 6, wherein the frame has a rail upon which the radiation source moves, and wherein the controller controls movement of the radiation source along the rail, so that transmission inspection can be performed on a plurality of portions of the inspected aircraft.

8. The system according to claim 6, wherein the detector has a length larger than or equal to two thirds of a width of the portal-framed structure.

9. The system according to claim 1, wherein the radiation source emits a first beam of X-ray/Gamma ray radiation having a first energy and a second beam of X-ray/Gamma ray radiation having a second energy, and wherein the detector receives the first and second beams of X-ray/Gamma ray radiation, and wherein the image generation module receives the output signal from the detector and generates a dual-energy transmission image of the inspected aircraft.

10. The system according to claim 1, wherein the detector comprises a first array of detectors that respond to a first portion of a beam of X-ray/Gamma ray radiation and a second array of detectors that respond to a second portion of the beam of X-ray/Gamma ray radiation and are arranged under the first array of detector, and wherein the image generation module receives the output signals of the first and second arrays of detectors and generates a pseudo dual-energy transmission image of the inspected aircraft.

11. The system according to claim 1, wherein the support of the frame comprises a rail, wherein the radiation source emits a beam of first-angle X-ray/Gamma ray radiation and a beam of second-angle X-ray/Gamma ray radiation, and wherein the detector comprises an array of first-angle detectors and an array of second-angle detectors that receive a beam of X-ray/Gamma ray first-angle radiation and a beam of second-angle X-ray/Gamma ray radiation that pass through the inspected aircraft, respectively, the array of first-angle detectors and the array of second-angle detectors each being arranged in respective trenches at a predetermined interval substantially parallel to the rail, and wherein the image generation module receives the output signals from the array of first-angle detectors and the array of second-angle detectors and generates dual-energy transmission images of the inspected aircraft.

12. The system according to claim 1, wherein the frame has a height that is adjustable.

13. A method for inspecting an aircraft, comprising steps of:
emitting a beam of X-ray/Gamma ray radiation from a radiation source, wherein the radiation source is mounted on a portal-framed structure, the frame comprises a support and a rail on the support, and the radiation source is movable on the rail;
receiving and converting the beam of X-ray/Gamma ray radiation to an output signal by a detector arranged in a trench that is co-planar with the beam of X-ray/Gamma ray radiation emitted from the radiation source;
controlling the radiation source to emit a beam of X-ray/Gamma ray radiation as an aircraft to be inspected moves through a scanning region constituted by the radiation source and the detector, and controlling the detector to receive a beam of X-ray/Gamma ray radiation emitted from the radiation source that has passed through the inspected aircraft; and
receiving the output signal from the detector to generate a vertical transmission image of the inspected aircraft.

14. The method according to claim 13, further comprising steps of:
controlling the movement of the radiation source along a rail to a predetermined position corresponding to a portion of the aircraft to be inspected, and synchronously controlling the detector to move to a position corresponding to the predetermined position of the radiation source so that a transmission inspection is performed on the portion of the aircraft.

15. A system for inspecting an aircraft, comprising:
a frame comprising a support;
at least two radiation sources configured to emit a beam of X-ray/Gamma ray radiation, the at least two radiation sources being mounted on the support frame and emitting beams of X-ray/Gamma ray radiation, wherein said beams are co-planar with each other;
a detector configured to receive and convert the beam of X-ray/Gamma ray radiation to an output signal, wherein the detector is arranged in a trench that is co-planar with the beam of X-ray/Gamma ray radiation emitted from the radiation sources;
a controller connected to the detector and the at least two radiation sources and configured to control the at least two radiation sources to emit a beam of X-ray/Gamma ray radiation as an aircraft to be inspected moves through a scanning region constituted by the at least two radiation sources and the detector, and to control the detector to receive beams of X-ray/Gamma ray radiation emitted from the at least two radiation sources that have been attenuated by the inspected aircraft; and
an image generation module configured to receive the output signal from the detector and generate a top-down transmission image of the inspected aircraft.

* * * * *